US00PP25531P2

(12) United States Plant Patent
Moy et al.

(10) Patent No.: US PP25,531 P2
(45) Date of Patent: May 12, 2015

(54) ***CITRUS* PLANT NAMED 'GREMOY79'**

(50) Latin Name: *Citrus reticulata*
Varietal Denomination: Gremoy79

(71) Applicant: Greenleaf Nursery Co., Park Hill, OK (US)

(72) Inventors: Ying Doon Moy; Larry Stein, Uvalde, TX (US)

(73) Assignee: Greenleaf Nursery Co., Park Hill, OK (US)

( * ) Notice: Subject to any disclaimer, the term of this patent is extended or adjusted under 35 U.S.C. 154(b) by 142 days.

(21) Appl. No.: 13/694,706

(22) Filed: Dec. 26, 2012

(51) Int. Cl.
*A01H 5/08* (2006.01)

(52) U.S. Cl.
USPC ..... Plt./202; Plt./201

(58) Field of Classification Search
CPC ..... A01H 5/0806
USPC ..... Plt./201, 202
See application file for complete search history.

*Primary Examiner* — Kent L Bell
(74) *Attorney, Agent, or Firm* — Penny J. Aguirre

(57) ABSTRACT

A new cultivar of *Citrus* tree, 'Gremoy79', that is characterized by its cold hardiness and its fruit with few seeds, an easy to peel skin, and a sweet, tart flavor, and its upright rounded plant habit.

2 Drawing Sheets

Botanical classification: *Citrus reticulata.*
Varietal denomination: 'Gremoy79'.

CROSS REFERENCE TO A RELATED APPLICATION

This application is co-pending with a U.S. Plant Patent Application filed for a plant derived from the same breeding program that is entitled *Citrus* Tree Named 'Gremoy47' (U.S. Plant Patent No. 23,496).

BACKGROUND OF THE INVENTION

The present invention relates to a new and distinct cultivar of satsuma mandarin tree, botanically known as *Citrus reticulata* 'Gremoy79', referred to hereafter by its cultivar name, 'Gremoy79'.

The new cultivar was derived from a controlled breeding program conducted by the Inventors in San Antonio, Tex., U.S.A. The overall purpose of the breeding program is the creation of Satsuma (mandarins) and tangerine hybrids that exhibit the fruit quality of Satsumas and the cold tolerance of select cold hardy tangerine varieties.

'Gremoy79' was selected by the Inventors in 2005 as a single unique tree that resulted from embryo rescue of a seed obtained from a cross made by the Inventors in 1998 between *Citrus reticulata* 'Changsha' (not patented), a tangerine, and an unnamed seedling of *Citrus reticulata* var. *unshiu* (syn, *Citrus unshiu*, not patented), a manderin, as the male parent.

Asexual propagation of the new cultivar was first accomplished by stem cuttings in San Antonio, Tex. in 2005 by one of the Inventors. Asexual propagation by stem cuttings has been determined that the characteristics of this cultivar are stable and are true to type in successive generations.

SUMMARY OF THE INVENTION

The following traits have been repeatedly observed and represent the characteristics of the new cultivar of *Citrus.*

1. 'Gremoy79' has been observed to be cold hardy to at least 9° F. (defoliation occurs at temperatures below about 15° F., foliage is evergreen above about 15° F.)
2. 'Gremoy79' exhibits fruit that is similar in quality to high quality Satsuma type *Citrus* trees with few seeds present (0 to 4 per fruit).
3. 'Gremoy79' exhibits fruit with an easy to peel skin.
4. 'Gremoy79' exhibits fruit with a sweet and tart flavor.
5. 'Gremoy79' exhibits on upright, rounded, bushy plant habit.

'Gremoy79' is readily distinguished from its female parent plant, 'Changsha'. Although 'Changsha' exhibits slightly better cold hardiness, the fruit of 'Gremoy79' is much improved, as the fruit of 'Changsha' is less flavorful, has abundant seeds, and more difficult to peel. In comparison to the male parent, a satsuma type seedling selection, 'Gremoy79' is more cold hardy and the flavor of 'Gremoy79' fruit is more tart. 'Gremoy79' can be most compared to *Citrus retuculata* var. *unshiu* 'Seto' (not patented) and 'Gremoy47'. 'Seto' differs from 'Gremoy79' in being less cold hardy. 'Gremoy47' differs from 'Gremoy79' in having a rounded globe plant habit, in being shorter in height and in being less cold hardy.

BRIEF DESCRIPTION OF THE DRAWINGS

The accompanying color photographs illustrate the distinguishing characteristics of the new cultivar 'Gremoy79'. The photographs were taken of the tree and fruit of an 7 year-old tree as grown in Uvalde, Tex.

Figure 1:
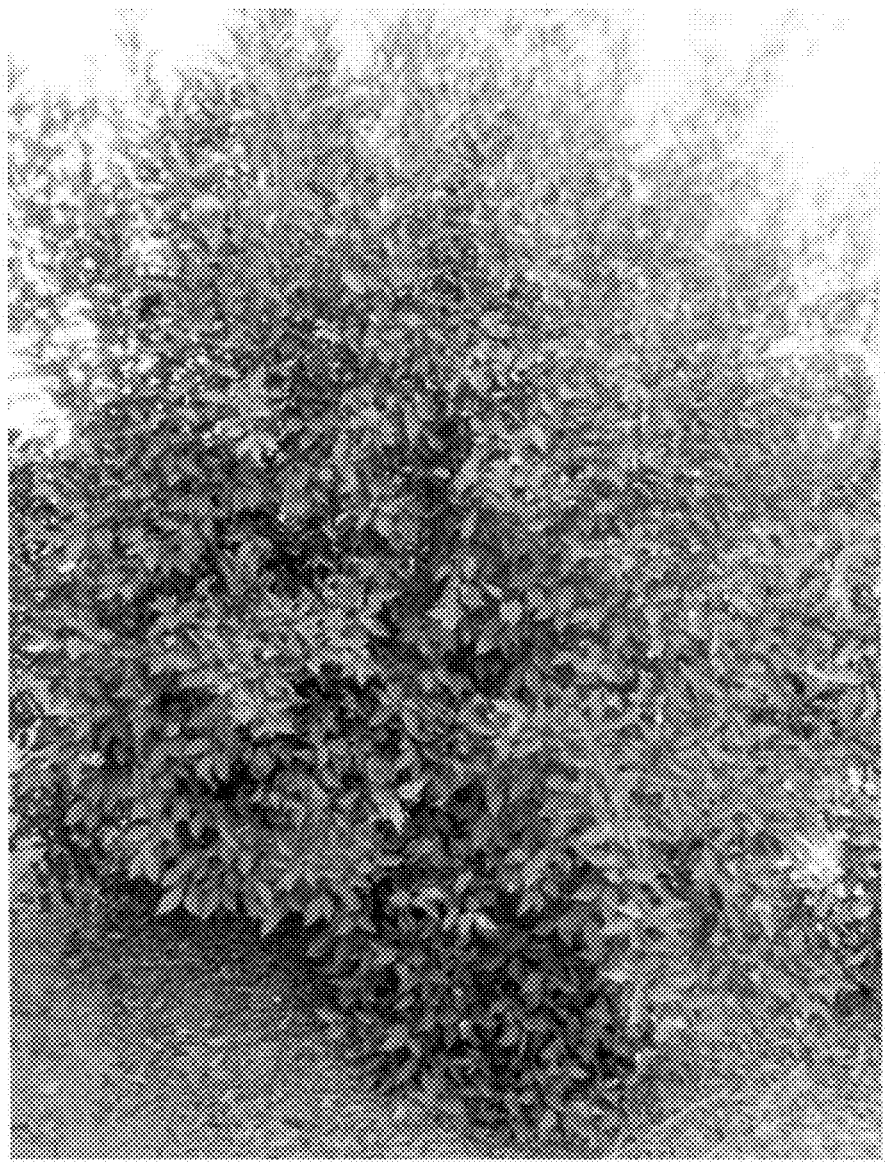
FIG. 1 shows a tree of 'Gremoy79'.
Figure 2:
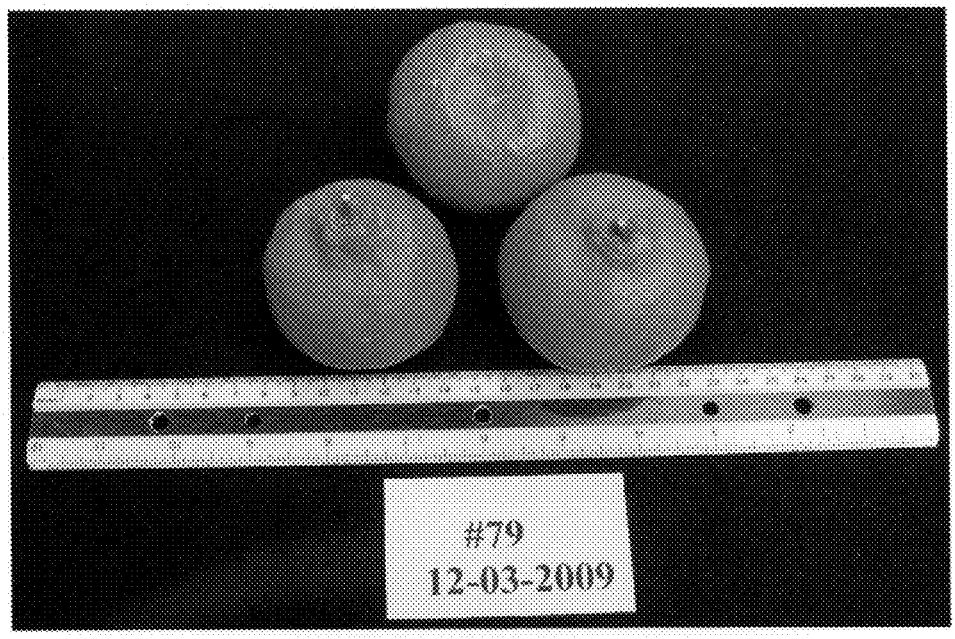
FIG. 2 shows three entire fruits of 'Gremoy79'.
Figure 3:
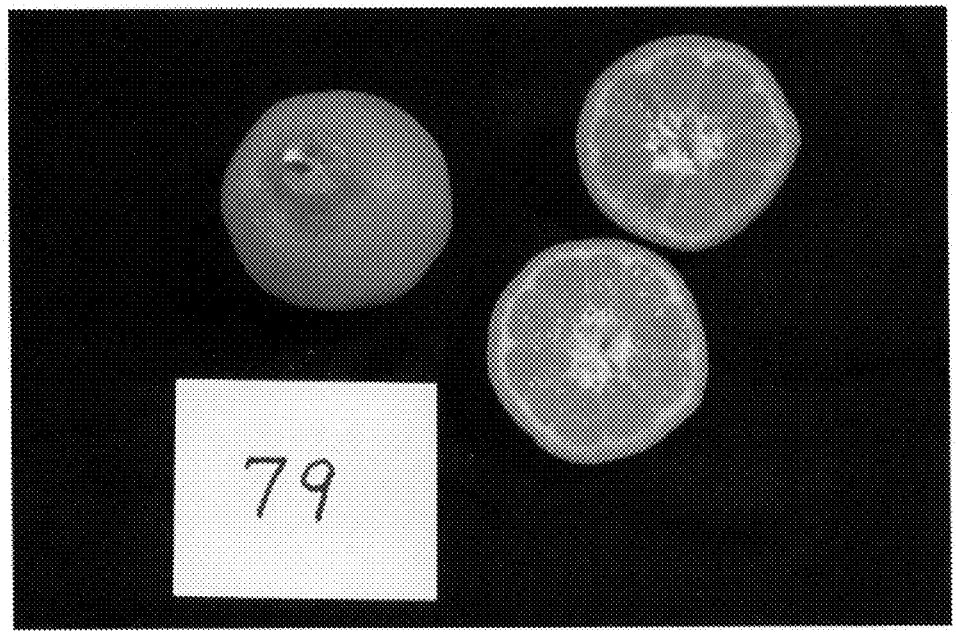
FIG. 3 shows a one entire fruit and a cross section of a cut fruit of 'Gremoy79'.

The colors in the photographs are as close as possible with digital photography techniques available, the color values cited in the detailed botanical description accurately describe the colors of the *Citrus.*

DETAILED BOTANICAL DESCRIPTION

The following is a detailed description of five year-old plants of 'Gremoy79' as grown outdoors in the ground in El Campo, Tex. with measurements of mature trees taken from plants grown in a trial plot at Uvalde, Tex. for a period of 7 years. The phenotype may vary somewhat with variations in temperature, day length, light intensity, soil types and water and fertility levels, without, however, any variance in the genotype. The color codes numbers refer to The 2007 Royal Horticultural Society's Colour Chart, London, England; except when general color terms of ordinary dictionary significance are used.

Tree description:

*Tree type.*—Sub-tropical shrub, evergreen.

*Tree habit.*—Upright, rounded, bushy plant habit.

*Tree size.*—Reaches 4.6 meters in height and 3.6 meters in width.

*Trunk description.*—Multi-stemmed from base, a seven year-old plant has an average of 6 main branches from base; average of 5.7 cm in diameter observed 30 cm above soil level.

*Growth rate.*—Moderate.

*Diseases resistance.*—No unique susceptibility or resistance has been observed when grown with other satsumas/tangerines cultivars.

*Pest resistance.*—*Citrus reticulata* when grown outdoors has few pest problems. No pest problems have been observed for the new cultivar, however resistance to any particular pest cannot be claimed.

*Hardiness.*—At least U.S.D.A. Zone 8A, has been found to be hardy to 9° F. and remains evergreen to about 15° F.

*Propagation.*—Stem cuttings or budding onto rootstock.

*Branching habit.*—Moderately branched, at approximately 45° from main stem.

*Branch strength.*—Strong.

*Branch surface.*—Smooth on new growth and becoming sandpaper-like (rough to touch) with irregular fine ridges in 3 to 4 years.

*Internode length.*—Average of 2.5 cm.

*Bark color of tree trunk.*—147A throughout, covered in a thin layer of bark 199D in color, thickened bark turns 199D in roughest and mature sections.

Description of dormant shoots:

*Stem appearance.*—Round to slightly oval.

*Stem strength.*—Strong and flexible, not brittle.

*Shine of bark.*—Matte finish.

*Stem size.*—Highly variable in length and 9 mm in width.

*Stem surface.*—Smooth bark for the first 2 years, then becoming finely ridged.

*Stem internode length.*—Average of 2.5 cm.

*Stem color.*—199B striated with 147A.

*Shoot angle.*—Approximately 45°.

Description of growing shoots:

*Color of shoot.*—Emerging 138A, mature between N199B and 147A.

*Shoot size.*—Highly variable in length and an average of 3 mm in width.

*Surface.*—Glabrous.

Leaf description:

*Leaf orientation.*—Upward to outward with aspect slightly cupped inward.

*Leaf division.*—Simple.

*Leaf shape.*—Elliptic.

*Leaf arrangement.*—Irregular.

*Leaf size.*—Average of 10.8 cm in length and 4.8 cm in width (leaves are smaller under intense sun light.

*Leaf apex.*—Acuminate.

*Leaf base.*—Cuneate.

*Leaf surface.*—Glabrous and satiny, speckled with minutely translucent glands.

*Leaf texture.*—Thick and leathery.

*Leaf margin.*—Finely crenulate.

*Leaf color.*—Upper surface emerging leaves 146A, mature leaves 147A; lower surface emerging leaves 146C, mature leaves 147B.

*Leaf venation.*—Pinnate, upper surface 147C in color, lower surface prominently raised main vein and slightly raised lateral veins, 146C in color.

*Petiole.*—Slightly winged near leaf base, average of 1.3 cm in length, 2 mm in diameter, wings 0.5 mm in width, 147A in color, glabrous surface.

*Durability of foliage to stress.*—Returns from wilt with no damage, resists wind and desiccation.

*Thorns.*—Frequent, attachment is superior to leaf petiole and lateral to bud, average of 1 cm in length, 0.5 to 2 mm in diameter, 146A at base, 164A towards apex.

Flower description:

*Flowering period.*—About 2 weeks in spring in Texas (first bloom commencing mid March, average of March 15th), timing is temperature dependent.

*Number of flowers.*—1 to 2 per node.

*Inflorescence type.*—Single flowers from axillary nodes.

*Flower buds.*—Oblong in shape, NN155C in color, about 1 cm in length and 7 mm in diameter.

*Flower size.*—Average of 3.5 cm in diameter, an average of 2 cm in depth.

*Flower fragrance.*—Mildly sweet, gardenia-like.

*Flower aspect.*—Upright and outward.

*Petals.*—5 per flower, un-fused, elliptic in shape and recurved, acute apex, truncate base, entire margin, about 1.8 cm in length and 5 mm in width, color of upper and lower surface NN155C, surface is satiny and glabrous, thick substance.

*Sepals.*—5, about 2 mm in width and 1.5 mm in length, fused with an small acute apex on each, N144A in color on upper and lower surface, waxy surface, triangular in shape, entire margin, curled inward around nectary, fused base, calyx is 5 mm in diameter, 1.5 mm in depth and circular in shape.

*Pedicel.*—144A in color, average of 1.5 cm in length and 1.5 mm in width, waxy surface.

*Pistil.*—1, 1 cm in length, style is 150C in color and 8 mm in length, stigma is 4B in color and globose in shape, ovary is globose in shape, inferior, about 2.5 mm in diameter, waxy in appearance and 144A in color, nectary is disk-shaped, 3 to 4 mm in diameter, 1 mm in depth, 150C in color, waxy surface.

*Stamens.*—About 16 per flower, filaments are fused into upright ring, 155C in color, and about 8 mm in length, anther is oblong in shape, 7A in color and 1.5 to 2 mm in length, pollen is dry and powdery and 21A in color.

Fruit description:

*Fruit harvest.*—First picking is generally mid November (average date November $15^{th}$) if temperature have been cool for sufficient sugar development, last picking is generally late December just prior to freezing temperatures (average date December $27^{th}$).

*Fruit type.*—Hesperidium.

*Fruit size.*—Average of 6.5 cm in diameter, 4.5 cm in height.

*Fruit shape.*—Oblate.

*Fruit symmetry.*—Roughly symmetrical from left to right hemisphere, top to bottom hemisphere varies with medium nipple-like protrusion at stem end vs. smoothly rounded concave depression at base of fruit.

*Fruit flavor.*—Sweet and tart.

*Fruit weight.*—Average of 110 grams.

*Fruit aroma.*—Orange scented.

*Fruit flesh color.*—N25A with carpel partitions 155B.

*Color of albedo.*—20B.

*Flesh texture.*—Glossy, juicy, slight indentations.

*Navel presence.*—None.

*Skin* (*rind*).—Easy to peel, 5 mm in thickness, outer layer (exocarp); rugulose, slightly glossy, 28B with oil glands (small pits) of 28A (N137A when immature), about 2 mm in thickness, inner surface (mesocarp or albedo); fibrous, 20B in color, about 2 mm in thickness.

*Fruit segments.*—10, kidney-shaped, an average of 4.5 cm in length and 1.5 cm in width.

*Fruit brix.*—Average of 13.

*Fruit set.*—Medium, fruit set is heavily dependent on early spring weather during bloom.

*Seed.*—0 to 1 seeds per section and 0 to 4 seeds per fruit.

*Cropping frequency.*—Annually.

*Juice production.*—Average of 70 ml per fruit.

*Fruit keeping quality.*—About 4 weeks at room temperatures before rind begins to mummify and fruit volume begins to shrink from dehydration, 6 to 8 weeks if refrigerated with humidity control.

*Fruit shipping quality.*—Thin skinned, soft and fragile; packing materials must be used to provide structural support and even weight distribution.

*Fruit use.*—Primarily for fresh consumption but may have potential for commercial juicing.

It is claimed:

1. A new and distinct variety of *Citrus* tree named 'Gremoy79' as described and illustrated herein.

* * * * *